United States Patent [19]
Weiss

[11] Patent Number: 5,184,616
[45] Date of Patent: Feb. 9, 1993

[54] APPARATUS AND METHOD FOR GENERATION OF VARYING WAVEFORMS IN ARRHYTHMIA CONTROL SYSTEM

[75] Inventor: Steven M. Weiss, West Pymble, Australia

[73] Assignee: Telectronics Pacing Systems, Inc., Englewood, Colo.

[21] Appl. No.: 780,757

[22] Filed: Oct. 21, 1991

[51] Int. Cl.⁵ .............................................. A61N 1/39
[52] U.S. Cl. ........................... 128/419; 128/419.01 G
[58] Field of Search ..................... 128/419 D, 419 PG

[56] References Cited

U.S. PATENT DOCUMENTS

| | | | |
|---|---|---|---|
| 2,004,751 | 6/1935 | Fischer et al. | 128/420 R |
| 3,460,542 | 8/1969 | Gemmer | 128/419 PG |
| 3,618,615 | 11/1971 | Greatbatch | 128/419 PG |
| 3,845,773 | 11/1974 | Fontaine et al. | 128/419 PG |
| 3,857,398 | 12/1974 | Rubin | 128/419 D |
| 3,886,931 | 6/1975 | Roslen | 128/420 R |
| 3,886,950 | 6/1975 | Ukkestad et al. | 128/419 D |
| 4,090,519 | 5/1978 | Pantridge et al. | 128/419 D |
| 4,637,397 | 1/1987 | Jones et al. | 128/419 D |
| 4,768,512 | 9/1988 | Imran | 128/419 D |
| 4,821,723 | 4/1989 | Baker, Jr. et al. | 128/419 D |
| 4,827,936 | 5/1989 | Pless et al. | 128/419 D |
| 4,850,357 | 7/1989 | Bach, Jr. | 128/419 RD |
| 4,869,252 | 9/1989 | Gilli | 128/419 D |
| 4,940,054 | 7/1990 | Grevis et al. | 128/419 PG |
| 5,014,697 | 5/1991 | Pless et al. | 128/419 D |

FOREIGN PATENT DOCUMENTS

| | | | |
|---|---|---|---|
| 0272021 | 7/1964 | Australia | 128/419 D |
| 24387/88 | 4/1989 | Australia . | |
| 1076286 | 2/1960 | Fed. Rep. of Germany | 128/419 D |

OTHER PUBLICATIONS

Schwingshackl et al. "Biomedical Engineering" vol. 8, No. 11, Nov. 1973, pp. 472-474.
O. Z. Roy et al., "A More Efficient Waveform for Cardiac Stimulation", *Medical and Biological Engineering*, vol. 9, pp. 495-501 (1971).
L. A. Geddes et al., "Principles of Applied Biomedical Instrumentation", p. 507, Published by John Wiley & Sons, New York (1989) 3rd Edition.
H. P. Schwan et al., "The Conductivity of Living Tissues", *Annals of the New York Acvadamy of Sciences*, vol. 65, pp. 1007-1013, (1956-1957).
D. Witzel et al., "The Influence of Cycle Frequency on the Effectiveness of Electrical Defibrillation of the Canine Ventricles", *Cardiovascular Research Bulletin*, vol. 5, pp. 112-118, (1967).

Primary Examiner—William E. Kamm
Attorney, Agent, or Firm—Gottlieb, Rackman & Reisman

[57] ABSTRACT

An implantable device and method for providing antiarrhythmia therapy to, and including arrhythmia in, a patient's inadequately functioning heart are disclosed. A pacemaker, defibrillator and microprocessor are utilized in conjuction with an electrode lead system adapted to be connected to the heart for providing the therapy and for inducing arrhythmia. Circuitry is employed in the pacemaker and defibrillator to generate respective trains of spaced pulses for delivery to corresponding portions of the electrode lead system, and a smoothing filter is provided in series with the trains of pulses to smooth each of the trains of pulses into discrete single pulse having a continuous waveform. The spacing, durations and polarities of the pulses in the trains are selectively variable so that the waveforms of the discrete single pulses can be selectively varied to provide diferent waveforms therein, in accordance with the needs of the patient and the programming of the device.

50 Claims, 9 Drawing Sheets

APPARATUS AND METHOD FOR GENERATION OF VARYING WAVEFORMS IN ARRHYTHMIA CONTROL SYSTEM

TECHNICAL FIELD

This invention relates to implantable medical devices which monitor the cardiac state of a patient by sensing the patient's intrinsic cardiac rhythm, particularly for the presence of tachyarrhythmias, and which deliver therapy in the form of electrical energy to cardiac tissue in an attempt to revert such tachyarrhythmias and restore the heart to a normal sinus rhythm.

In particular it relates to an apparatus and method for the generation of varying waveforms in an implantable medical device which is capable of both delivering defibrillation therapy to a patient's inadequately functioning heart and performing the induction of fibrillation and other arrhythmias therein. Preferably, the implantable defibrillator also has the capability of delivering bradycardia and antitachycardia pacing therapies when necessary.

PRIOR ART

U.S. Pat. No. 3,857,398 to Rubin describes a combined pacemaker/defibrillator. This device either performs a bradycardia pacing or a defibrillation function depending on the detection of a ventricular tachycardia or a ventricular fibrillation (VT/VF). If a VT/VF is detected, the device is switched to the defibrillating mode. After a period of time to charge the capacitor, a defibrillation shock is delivered to the patient. This device has no provision for antitachycardia pacing and is unable to provide fibrillation/arrhythmia induction either through the pacing circuitry or the defibrillation circuitry. Furthermore, the device disclosed contains no provision for varying the shape of the defibrillation or pacing waveform.

A multiprogrammable, telemetric, implantable defibrillator is disclosed in copending patent application Ser. No. 576,178 to N. L. Gilli et al., entitled "Reconfirmation Prior to Shock for Implantable Defibrillation," filed Aug. 29, 1990. The Gilli et al. device contains a bradycardia support system as well as a high energy shock system to revert ventricular tachycardias to normal sinus rhythm. On reconfirmation of the presence of a tachycardia, a shock is delivered to the patient either at a predetermined time or when the desired energy level is reached. This implantable pacemaker/defibrillator does not include an antitachycardia pacing facility. It cannot be used to induce either ventricular tachycardias or ventricular fibrillations by delivering a rapid succession of either pacing pulses through the pacing circuitry or micro-shocks via the defibrillation circuitry. Furthermore, there is no provision in the device for generation of waveforms from the defibrillation circuitry, other than truncated exponential waveforms.

A further development in the field of combined implantable devices is described in U.S. Pat. No. 4,940,054 to R. Grevis et al., entitled "Apparatus and Method for Controlling Multiple Sensitivities in Arrhythmia Control Systems Including Post Therapy Pacing Delay". This device is a microcomputer based arrhythmia control system which is programmable by means of a telemetric link. The device provides single chamber bradycardia support pacing, antitachycardia pacing, and cardioversion or defibrillation shocks for restoring normal sinus rhythm to a patient. This implantable pacemaker/defibrillator device incorporates a facility to induce ventricular fibrillation and ventricular tachycardia. This is for the purpose of testing and evaluating the effectiveness of the programmed therapy. This induction is achieved by rapid pacing pulses via the pacing circuitry. Although capable of delivering multiple defibrillation shocks in succession either manually or automatically, the device is not able to provide more than one type of waveform by means of the defibrillation circuitry, which takes the form of truncated exponential capacitor discharges. Similarly, the pacing circuitry is limited to one type of waveform.

U.S. Pat. No. 4,821,723 describes a variation of the defibrillation waveform, involving a reversal of the phase of the defibrillatory shock during the delivery of the shock to the heart. Though this waveform can be multi-phasic, each phase is still in the form of a truncated exponential.

Some existing defibrillators provide a relative variation of the defibrillation waveform when delivering the defibrillatory shock to multiple electrodes. In this case the shape of each of the resultant waveforms produced by means of a particular electrode configuration, although different relatively from the waveform produced at each of the other electrode configurations, is, however, still based on the truncated exponential capacitor discharge waveform.

The waveshape of the pacing pulse in existing devices is based on capacitor-discharged, truncated, exponential waveform technology, although the voltage droop that occurs tends to be less than that which occurs in the case of a defibrillation pulse, and more closely approaches a square wave.

Thus, existing pacemaker devices, including pacemaker/defibrillators when delivering pacing pulses, are not able to deliver pacing pulses which have selectable or variable waveforms.

A variant on the pacing pulse may be attainable by means of a slow ramp-up in voltage prior to the delivery of the pulse, such that the net delivered charge is zero. Charge balancing, such as this, is a means of minimizing polarization of the electrode-tissue interface. Polarization occurs when there is a charge difference across a boundary of differing electrical impedances. In order to stimulate cells across a polarized boundary, the polarization potential must first be overcome in order to deliver the required stimulus voltage to the cells.

This raises the required voltage for stimulating cells and, as such, increases the size of implantable pacemakers and defibrillators and decreases the longevity of the batteries within such devices. Maintaining a polarization potential across such a boundary also increases the risk of damage to the underlying cells.

An important consideration in increasing patient safety, increasing implantable pacemaker and defibrillator longevity and decreasing the size of the implant, is the ability to decrease the amount of polarization occurring not only at the electrode-tissue interface, but also at the interface of each cell membrane in the current path between the electrodes. In an article by O. Z. Roy and R. W. Wehnert, entitled "A More Efficient Waveform for Cardiac Stimulation", appearing in Medical and Biological Engineering, Vol. 9, pages 495-501 (1971), it was found that "the rising sawtooth produces what seems to be a better matching between the electrode and electrolyte . . ." "This tends to indicate that the polarization effects are lower for a rising sawtooth."

Roy and Wehnert were limited in their approach to overcoming the effects of polarization as they only concerned themselves with sawtooth waveforms and their effects on pacing.

However, prior art implantable pacemaker/defibrillators generally have not been able to generate this type of waveform for use in an implantable device.

The relationship between efficient energy transfer and a particular type of waveform is described in a book by L. A. Geddes and L. E. Baker, entitled "Principles of Applied Biomedical Instrumentation", 3rd edition, Wiley-Interscience, 1989, at p. 507. An approximate equivalent circuit of the electrodes and heart tissue set-up as used in internal defibrillation is shown. Of particular interest is the equivalent circuit for living tissue. This circuit incorporates a capacitor in parallel with part of the tissue resistance. From the equation for capacitance $I = C \, (dV/dT)$, it can be seen that for a rapidly rising voltage across the tissue (that is, a large $dV/dT$), as in the leading edge of a truncated exponential discharge, most of the current delivered to the tissue is shunted across this capacitance with very little current being delivered to the resistive load of the tissue in parallel with it. As the capacitor charges up, however, $dV/dT$ decreases as does the current I, and more current passes through the resistive load of the tissue. Ultimately, it is desirable for all of the current to pass through the resistive load and none through the capacitive load. To achieve this, a low $dV/dT$ is required. This can be obtained with a slow leading edge to a pulse as in a sawtooth, sine, triangular or similar wave. Hence by decreasing the slope of the leading edge of a pulse, whether for pacing, defibrillation, fibrillation or other arrhythmia induction, or other electrical stimulus of biological tissue, a more efficient energy transfer can take place and a reaction to the stimulus can be achieved with a lesser energy requirement.

In further regard of a device capable of delivering more effective therapy or induction waveforms, the relationship between cycle frequency and effectiveness of electrical defibrillation is considered in an article by H. P. Schwan and C. F. Kay, entitled "The Conductivity of Living Tissues", published in The Annals of the New York Academy of Sciences, Vol. 65, pages 1007-1013 (1956-57). Here it is shown that the ratio of capacitive current flow to resistive current flow through the heart muscle increases for frequencies above 100 Hz. That is, capacitive or shunting current through the heart muscle increases as the frequency component of the signal becomes very high (as occurs in the leading edge of a truncated exponential capacitor discharge). Support for the hypothesis can also be found in a paper by D. Witzel, L. A. Geddes, J. McFarlane and W. Nichols, entitled "The Influence of Cycle Frequency on the Effectiveness of Electrical Defibrillation on the Canine Ventricles", and published in the Cardiovascular Research Centre Bulletin, Vol. 5, at pages 112-118 (1967). In this paper it is shown that defibrillation requires increasingly more energy to become effective when frequencies above 60 Hz are used. This also happens for frequencies below 60 Hz; however, the reason for this is that the duration of a single cycle of defibrillatory shock becomes so long that fibrillation is likely to be reinduced.

A lesser energy requirement to effect a stimulus, as described above, allows a reduction in the size of an implantable stimulus generator as well as an increase in longevity of the device. Reducing the size of such a generator is an important consideration as present implantable cardioverter/defibrillators are somewhat cumbersome and are uncomfortable in certain patient groups. In addition, by delivering the energy required for a stimulus such as defibrillation more efficiently, lesser energies are required and hence less damage to the heart results.

Waveforms with slow leading edges have not previously been used in implantable devices due to the difficulty of generation of these waveforms. In U.S. Pat. No. 4,090,519, a defibrillator circuit for producing a Lown waveform (damped sinusoid) defibrillation pulse is described. It is also stated therein that a large inductor of 50 millihenries is required to create the shape of the required waveform. For this reason, and because size restricts the use of large inductors, sinusoid waveforms have not been used in implantable devices. Waveforms other than truncated exponential have also not been used in implantable devices before due to the energy loss (in the form of heat) which occurs within the output amplifier circuitry. A transistor, regardless of type, dissipates substantial amounts of energy in the form of heat if it is not in either the fully on or fully off state.

Therefore, if a transistor is required to vary the amount of current passing through it, as would normally be required in the generation of a wave such as a sinusoid, a great deal of deliverable energy would be lost in heat from the circuit. For defibrillation purposes for example, where high current levels are required from the device, the loss of energy in the form of heat would not only risk damage to the transistors, but would reduce the effectiveness of the defibrillation shock. To counteract this, even more energy would be required from the device which, in turn, would further shorten the life of the transistors and the batteries. Furthermore, the device would be required to be much larger in order to accommodate larger capacitors and batteries.

U.S. Pat. No. 4,768,512 discloses an alternative method for the generation of waveforms other than truncated exponential, in which the energy available from charged capacitors is chopped and then the resultant waveform is smoothed with a filter in parallel with the load (heart). By varying the duty cycle of the chopper, any waveform can be generated. Furthermore, by chopping the charge on the capacitors, the transistors involved rapidly change from being fully on to fully off, and vice versa. Hence minimal energy is lost in the form of heat in the transistors.

The extra circuitry required for the creation of the arbitrary waveforms described above is small in size and is compensated for by a reduction in capacitor and battery size within an implantable pacemaker or defibrillator, due to the increased efficiency of the device.

The invention disclosed in U.S. Pat. No. 4,768,512 has several major deficiencies with regard to its usefulness, however. Firstly, the waveform generated by this device is only provided for defibrillation purposes and the device neglects any advantages that might result from the use of the waveform for pacing, arrhythmia induction and other biological stimulation. Secondly, the chopping is at a very high frequency which, as stated before, increases the energy requirement for successful defibrillation. Thirdly, this device chops the voltage which is applied from the storage capacitor to the implantable electrodes at a regular duty cycle and at a regular rate. It does not attempt to vary the shape of the voltage wave being delivered to the implantable electrodes. Finally, the chopped pulses are not smoothed and, as a result, are each seen by the heart as being very high in frequency, and consequently very high in threshold. Moreover, the slope of the wave does not compensate for the polarization effect caused by the large amplitude rapid edges of each chopped pulse.

It is also known in the technology that waveforms can be current-based or voltage-based.

Conventional technology for the delivery of pacing and defibrillation pulses is to charge a capacitor (or bank of capacitors) to a specified voltage, disable the charging circuitry, and connect the charged capacitors directly to the heart. The connection of the capacitors to the heart causes the capacitors to discharge their energy into the heart. Due to the relatively low impedance usually associated with the heart and the pacing or defibrillation electrodes, the capacitors discharge their energy into the heart exponentially and with a time constant proportional to a multiple of the value of the capacitance and the impedance of the heart-electrode system. As the discharge is exponential, however, the low energy tail end of the discharge has a long time course which can not only cause polarisation and cardiac damage problems, but can also induce cardiac arrhythmias. To account for this, the tail end of the discharge is truncated—usually at between 0.1 and 15 milliseconds.

Australian Patent Application No. 24387/88, published Apr. 27, 1989, discloses a non-invasive cardiac pacemaker with a relatively slow ramp on the leading edge. The rate of increase of the voltage on this ramp has been reduced from previously used high rates in order to lower the intensity of (skeletal) muscle stimulation associated with external non-invasive cardiac pacing. In a similar vein but with application to direct cardiac stimulation in contrast to non-invasive stimulation, the authors of the present invention have found experimentally that the application of direct cardiac stimulation by the use of slow leading edge waveforms, such as sine waves, produces considerably less thoracic muscle contraction than occurs with a fast leading edge waveform. The above device, being external, is not suitable for direct cardiac stimulation and is only capable of generating a single type of waveform for pacing. Accordingly, it is only applicable to cardiac pacing and is not capable of generating waveforms suitable for defibrillation, cardioversion, arrhythmia induction or other cardiac stimulation such as antitachycardia pacing.

Prior art devices to date have not been able to offer a device capable of producing arbitrary waveforms for direct cardiac stimulation which can be selected not only for their pain minimization, but also for their overall efficiency in cardiac stimulation.

Furthermore, in existing devices, it has been difficult to successfully achieve defibrillation and pacing therapy, as well as induced VF's or other arrhythmias, due to a limitation in the type of waveforms able to be delivered by the device. The inability to effectively induce VF's and other fibrillations or arrhythmias has therefore proved disadvantageous and not in the complete interest of patient safety because the individually physician-programmed therapies related to the least time-consuming therapy mode and the most effective defibrillation energy may not necessarily be tested and evaluated at the time of implant or patient follow-up.

OBJECTS OF THE INVENTION

It is, therefore, a primary object of the present invention to provide an improved implantable pacemaker defibrillator device capable of generating a plurality of different waveforms for use in providing successful defibrillation and cardioversion therapies, bradycardia pacing therapy and antitachycardia pacing therapy, along with fibrillation and other arrhythmia induction, thereby allowing efficient testing and evaluation of the foregoing therapies as well as other operations of the implantable device which may be required by a patient's physician.

It is also an object of the invention to provide an improved method and apparatus for generating and controlling micro-shock waveforms thus allowing the delivery of different types of micro-shock waveforms to the heart.

Another object of the invention is to provide a method and apparatus capable of delivering different types of electrical therapy waveforms to the heart for the purpose of pain minimization in patients.

A further object of the invention is to provide a device capable of generating varying waveforms in a patient by means of electrical stimuli delivered via the defibrillation circuitry, wherein the electrical stimuli take the form of defibrillation shocks, or cardioversion shocks, or micro-shocks delivered in rapid succession.

A still further object of the invention is to provide a device capable of generating varying waveforms in a patient by means of electrical stimuli delivered via the pacing circuitry, wherein the electrical stimuli take the form of pacing pulses.

Further objects and advantages of the invention will become apparent as the following description proceeds.

SUMMARY OF THE INVENTION

Briefly stated, and in accordance with one embodiment of the invention, an implantable device for providing therapy to a patient's inadequately functioning heart comprise defibrillation electrode lead system, means for detecting fibrillation of the heart, circuit means including charge storing means for applying electrical therapy to the heart via said electrode lead system, means responsive to the detection of a fibrillation condition for charging the charge storing means to an appropriate energy level for delivering defibrillation therapy to the patient's heart, and means coupled to the circuit means for selectively providing to the defibrillation electrode lead system pulses having any one of a plurality of different defibrillation waveforms.

In accordance with another aspect of the invention, an implantable device for providing therapy to a patient's inadequately functioning heart comprises a cardioversion electrode lead system, means for detecting arrhythmias of the heart, circuit means including charge storing means for applying cardioversion therapy to the heart via the electrode lead system, means responsive to the detection of an arrhythmia condition for charging the charge storing means to an appropriate energy level for delivering cardioversion therapy to the patient's heart, and means coupled to the circuit means for selectively providing to the cardioversion electrode lead system pulses having any one of a plurality of different cardioversion waveforms.

In accordance with yet another aspect of the invention, an implantable device for providing therapy to a patient's inadequately functioning heart comprises a pacing electrode lead system, means for detecting a bradycardia condition of the heart, circuit means for applying bradycardia pacing therapy to the heart via the electrode lead system, means responsive to a detected bradycardia condition for supplying power to the circuit means at an appropriate energy level for delivering the bradycardia pacing therapy to the patient's heart, and means coupled to the circuit means for selectively providing to the pacing electrode lead system pulses having any one of a plurality of different pacing pulse waveforms.

In accordance with a still further aspect of the invention, an implantable device for providing therapy to an inadequately functioning heart comprises a pacing electrode lead system, means for detecting a tachycardia condition of the heart, circuit means for applying antitachycardia pacing therapy to the heart via the electrode lead system, means responsive to a detected tachycardia condition for supplying power to the circuit means at an appropriate energy level for delivering the antitachycardia pacing therapy to the patient's heart, and means coupled to the circuit means for selectively providing to the pacing electrode lead system pulses having any one of a plurality of different pacing pulse waveforms.

In accordance with another aspect of the invention, an implantable device for providing therapy to an inadequately functioning heart comprises a defibrillation electrode lead system, means for detecting fibrillation of the heart, circuit means including charge storage means for applying defibrillation therapy to the heart via the electrode lead system, means for charging the charge storing means to an appropriate energy level for delivering the defibrillation therapy to the patient's heart, and arrhythmia induction means including means for providing in succession to the defibrillation electrode lead system a plurality of pulses having any of a plurality of different micro-shock waveforms.

In accordance with a still further aspect of the invention, an implantable device for providing therapy to an inadequately functioning heart comprises a cardioversion lead system, means for detecting arrhythmias of the heart, circuit means including charge storing means for applying cardioversion therapy to the heart via the electrode lead system, means responsive to the detection of an arrhythmia condition for charging the charge storing means to an appropriate energy level for delivering cardioversion therapy to the patient's heart, and arrhythmia induction means including means for providing in succession to the cardioversion electrode lead system a plurality of pulses having any of a plurality different micro-shock waveforms.

In accordance with yet another aspect of the invention, an implantable device for providing therapy to an inadequately functioning heart comprises a pacing electrode lead system, means for detecting arrhythmias of the heart, circuit means including charge storing means for applying pacing therapy to the heart via the electrode lead system, means responsive to the detection of an arrhythmia condition for charging the charge storing means to an appropriate energy level for delivering pacing therapy to the patient's heart, and arrhythmia induction means including means for providing in succession to the electrode lead system a plurality of pulses having any of a plurality of different pacing waveforms.

The implantable devices preferably include programmable means for altering the shapes of the pacing pulse, microshock and cardioversion and defibrillation shock waveforms, as well as programmable means for altering parameters such as amplitude, pulse or shock width, polarity, number of phases, number of pulses or shocks, timing intervals between pulses and/or shocks, timing intervals between an electrical, mechanical, chemical or other haemodynamic trigger and the delivery of a pulse and/or shock for each of the bradycardia pacing, antitachycardia pacing, cardioversion, defibrillation and micro-shock waveforms, selection of electrode combinations for each of bradycardia pacing, antitachycardia pacing, cardioversion, defibrillation and arrhythmia induction, and selection of single, simultaneous or sequential therapy by the pacing and cardioversion/defibrillation circuitry. Alternatively, some or all of these parameters may be determined automatically by the device.

BRIEF DESCRIPTION OF THE DRAWINGS

While the specification concludes with claims particularly pointing out and distinctly claiming the subject matter regarded as the invention herein, it is believed that the present invention will be more readily understood from the following description, taken in conjunction with the accompanying drawings, in which:

BEST MODE OF THE INVENTION

The term "fibrillation/tachyarrhythmia" as used herein refers to any fast abnormal rhythm of the heart which may be amenable to treatment by electrical discharges and specifically includes supraventricular tachycardia (SVT), atrial tachycardia (AT), ventricular tachycardia (VT), atrial flutter and fibrillation (AF), and ventricular flutter and ventricular fibrillation (VF).

In the apparatus and method disclosed the term "defibrillation" refers to the discharge of electrical energy into cardiac tissue in an attempt to terminate or revert a tachycardia, and may range from a high (40 Joules or more) to a low (less than 1 Joule) of energy discharge. The discharge may be monophasic or biphasic but is not restricted to these waveforms. Defibrillation shocks may or may not be synchronised to the rhythm of the heart.

"Cardioversion" is a particular example of defibrillation and generally refers to lower energy shocks in comparison to defibrillation, with the shock usually being synchronized to the patient's R-wave.

A "micro-shock" is defined in this description as a low level electrical stimulus, generally in the range of 5-15 volts, but in certain circumstances it may be as low as less than 1 volt and as high as 40 or more volts, and is delivered to the patient's heart through the defibrillation or cardioversion circuitry.

Micro-shocks are not delivered singly as is generally the case with higher energy cardioversion or defibrillation shocks, which have the purpose of reverting a tachyarrhythmia in a patient's heart so as to restore normal sinus rhythm. In contrast they are delivered in rapid succession, either continuously for a finite predetermined time interval or in association with a train of micro-shocks, in order to induce a condition of fibrillation or other arrhythmia in a patient's heart from a condition of normal sinus rhythm.

A "pacing pulse" is defined as being similar to a micro-shock, though generally lower in voltage, with the delivery of the pulse generally being initiated by the pacing circuitry instead of by means of the defibrillation circuitry.

Figure 1:
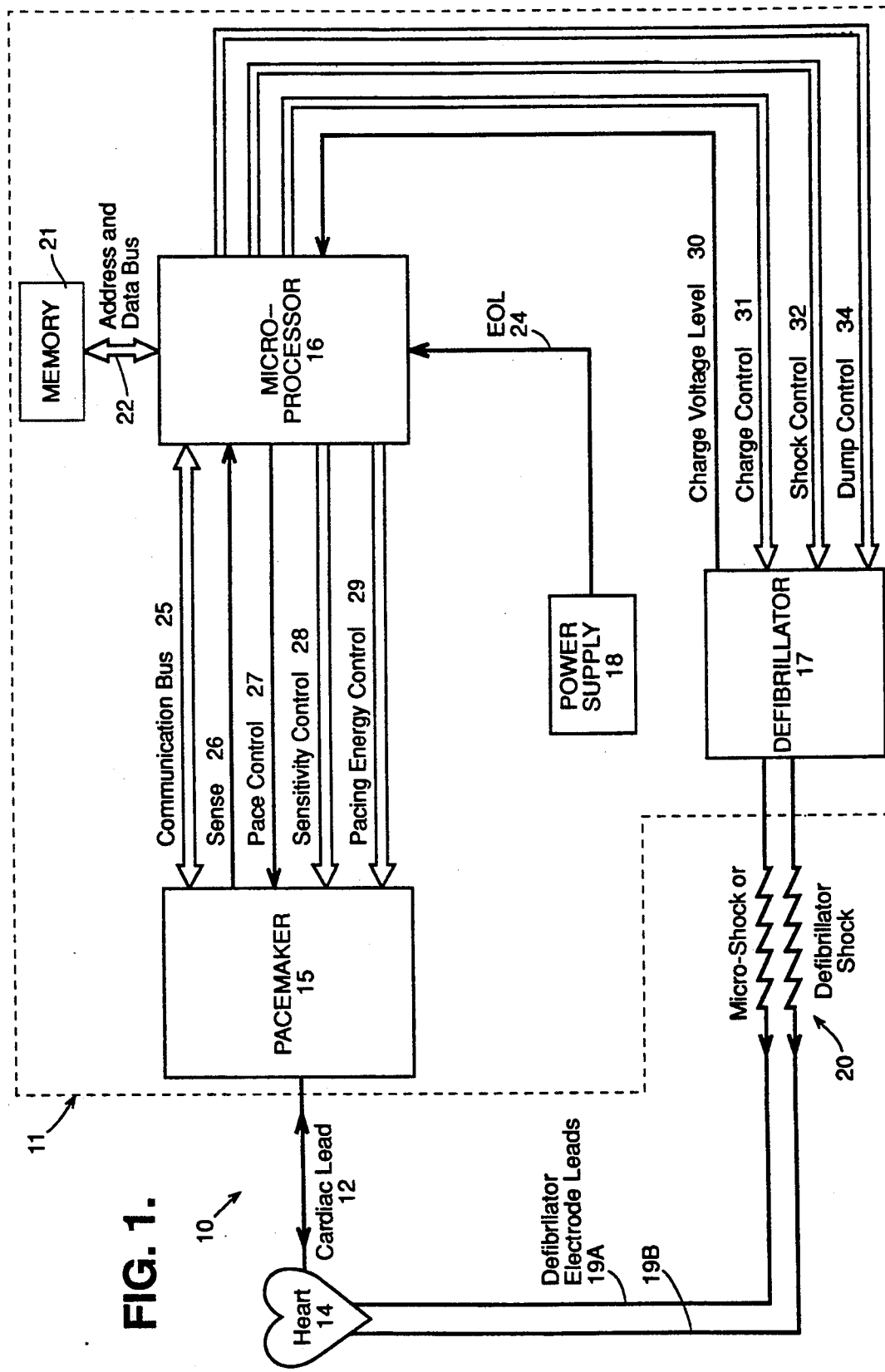
FIG. 1 is a block diagram of an arrhythmia control system in accordance with the present invention.

Referring to FIG. 1, there is depicted a block diagram of an arrhythmia control system 10. System 10 is designed to be implantable and includes a pulse module 11 and appropriate leads.

More particularly, system 10 will generally include a cardiac lead 12 extending to the atrium of a patient's heart 14 for the administration of therapy to the atrium, or extending to the ventricle of the patient's heart for the administration of therapy to the ventricle, or extending to both in the case of a dual chamber system. System 10 generally also includes a pacemaker 15 for the detection of analog signals representing cardiac electrical activity and for the delivery of pacing pulses to the heart; a microprocessor 16 which, in response to various inputs received from the pacemaker 15 as well as from a defibrillator 17, performs various operations so as to generate different control and data outputs to both pacemaker 15 and defibrillator 17; and a power supply 18 for the provision of a reliable voltage level to pacemaker 15, microprocessor 16 and defibrillator 17 by suitable electrical conductors (not shown).

Defibrillator 17 produces a high voltage to charge its capacitors and then discharges them in response to control signals from microprocessor 16. Defibrillator electrode leads 19A and 19B transfer the energy of a defibrillator shock or a micro-shock 20 from the implanted pulse module 11 to the surface of the heart 14. It is also possible to have one lead at one polarity while the pulse module case or can serves as an electrode of opposite polarity. Variations employing several different electrode configurations are also possible.

Microprocessor 16 is connected to an external memory 21 by an address and data bus 22. An end-of-life (EOL) signal line 24 is used to provide, to microprocessor 16, a logic signal indicative of the approach of battery failure in power supply 18.

As more fully described below, microprocessor 16 and pacemaker 15 are connected by a communication bus 25, a sense line 26, a pace control line 27, a sensitivity control bus 28, and a pacing energy control bus 29. As also more fully described below, microprocessor 16 is connected to defibrillator 17 by a charge voltage level line 30, a charge control bus 31, a shock control bus 32, and a dump control bus 34.

For purposes of this invention, it is noted that defibrillation, cardioversion and arrhythmia indication waveforms, all of which are generated in defibrillator 17 and have previously defined waveshapes, are preferably delivered to the ventricles of a patient's heart 14 via defibrillator electrode leads 19A and 19B. For this to take place, the defibrillator 17 is controlled by microprocessor 16 via a charge control bus 31, a shock control bus 32, a charge voltage level line 30 and a dump control bus 34. As more fully described below, microprocessor 16 delivers a signal to charge control bus 31 which, referring to FIG. 4, initiates charging of a capacitor 104 in defibrillator 17. After either a predetermined time or when the charge voltage level line 30 indicates by feedback to the micro-processor that a suitable charge has been obtained within capacitor 104, the microprocessor turns off the charge control signal 31 and turns on the shock control signal 32. Referring to FIG. 5, shock control signal 32 causes output shock control switches 106-109 in the high voltage circuits of defibrillator 17 to activate. After activating the shock control switches 106, 107, 108, and 109 for a predetermined time (in the order of hundreds of microseconds, or milli-seconds) and in a predetermined configuration of phases and electrodes, shock control signal 32 is turned off by the microprocessor. This sequence is repeated after a certain interval (again in the order of milliseconds, or hundreds of milliseconds), as controlled by a timer within microprocessor 16. Furthermore, each time the sequence is repeated, it may or may not be repeated in the same configuration.

In an alternative embodiment, it is possible for the defibrillation and/or cardioversion circuitry of defibrillator 17 (FIG. 1) to be electrically connected to the electrodes of pacing leads 12, as shown in copending patent application number . . . (Case 136), entitled "Apparatus and Method for Arrhythmia Induction in an Arrhythmia Control System", or conversely, for the pacemaking circuitry of pacemaker 15 to be electrically connected to the cardioversion and/or defibrillation electrodes 19A and 19B. For this, some additional circuitry (not shown) would be required for the appropriate switching of the outputs of pacemaker 15 or defibrillator 17 to leads 19A and 19B, or lead 12, respectively. Furthermore, additional circuitry would be required for protection of the circuitry discussed in this paragraph.

Figure 2:
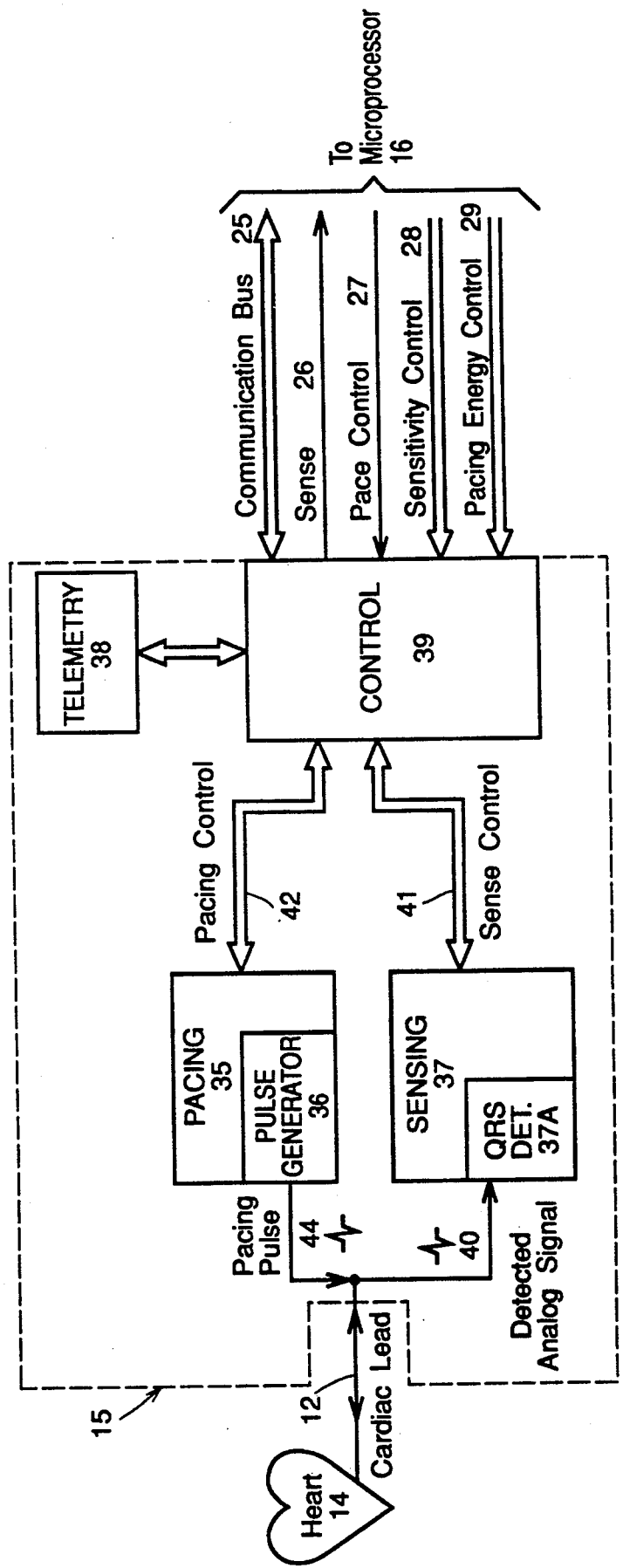
FIG. 2 is a block diagram of a pacemaker utilized in the system of FIG. 1.

Referring to FIG. 2, pacemaker 15 comprises a pacing circuit 35 which includes a pacing pulse generator 36. Pacemaker 15 also includes a sensing circuit 37, and a telemetry circuit 38. In addition, there is a control block 39 which includes an interface to microprocessor 16.

In operation, sensing circuit 37 detects analog signals 40 from the heart 14 in an internal QRS detector 37A and converts the detected signals to digital signals. Furthermore, sensing circuit 37 receives an input sense control signal (which determines the sensitivity of the detection circuits in sensing circuit 37) by way of a sense control bus 41 from control block 39. As more fully described below, a change in this sensitivity will affect the voltage deviation required at the sensing electrode for a sense to be registered.

Pacing circuit 35 receives inputs from control block 39, including a pace control and a pacing energy control, by way of a pacing control bus 42, which carries the signals received in control block 39 from pace control line 27 and pacing energy control bus 29. The pace control determines the type of pacing that will occur, while the magnitude of the pulse energy is determined by the pacing energy control. Pacing circuit 35 causes pulse generator 36 to generate pacing pulses 44 which are delivered to the patient's heart 14 by means of cardiac lead 12.

Figure 6:
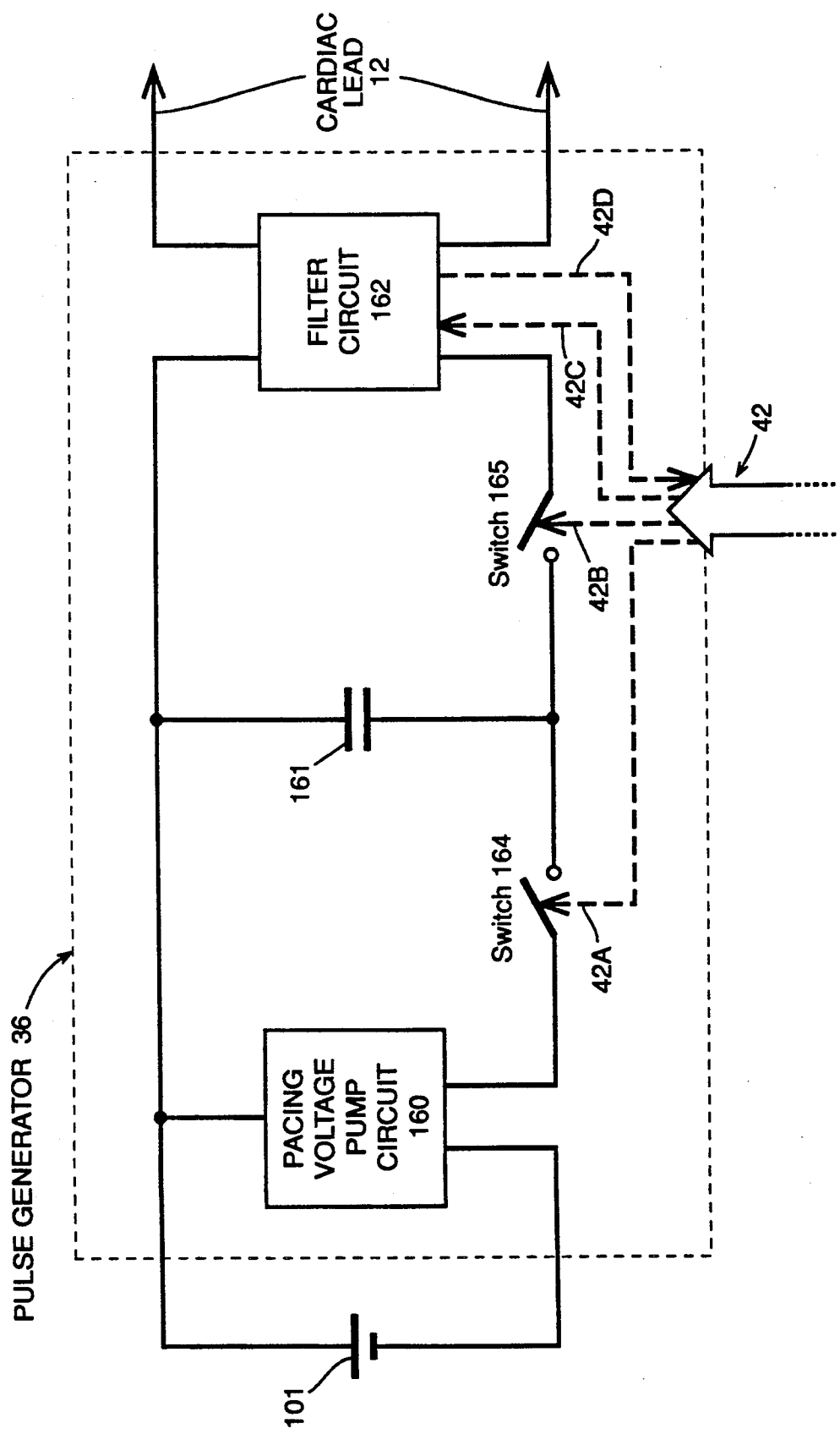
FIG. 6 is a schematic diagram of a pacing pulse generator utilized in the pacemaker of FIG. 2.

Referring briefly to FIG. 6 in conjunction with FIG. 2, and as will be described in greater detail hereinafter, pulse generator 36 includes a pacing voltage pump circuit 160 which charges a capacitor 161 to a suitable pacing voltage via a switch 164. Another switch 165, controlled by a signal from pacing control bus 42, repeatedly delivers small amounts of charge from capacitor 161 to a filter circuit 162, which controls the shape of the pacing waveform that is delivered to the patient's heart via cardiac lead 12. Control messages from the control block 39 are delivered to pulse generator 36 by pacing control bus 42. Similarly, feedback for the control of pulse generator 36 is transmitted to control block 39 by pacing control bus 42.

Telemetry circuit 38 (FIG. 2) provides a bi-directional link between control block 39 of pacemaker 15 and an external device such as a programmer. It allows data such as the operating parameters to be read from or altered in the implanted pulse module 11 (FIG. 1), and facilitates the programming of the waveshapes of the defibrillation, cardioversion, arrhythmia induction and pacing waveforms.

Figure 3:
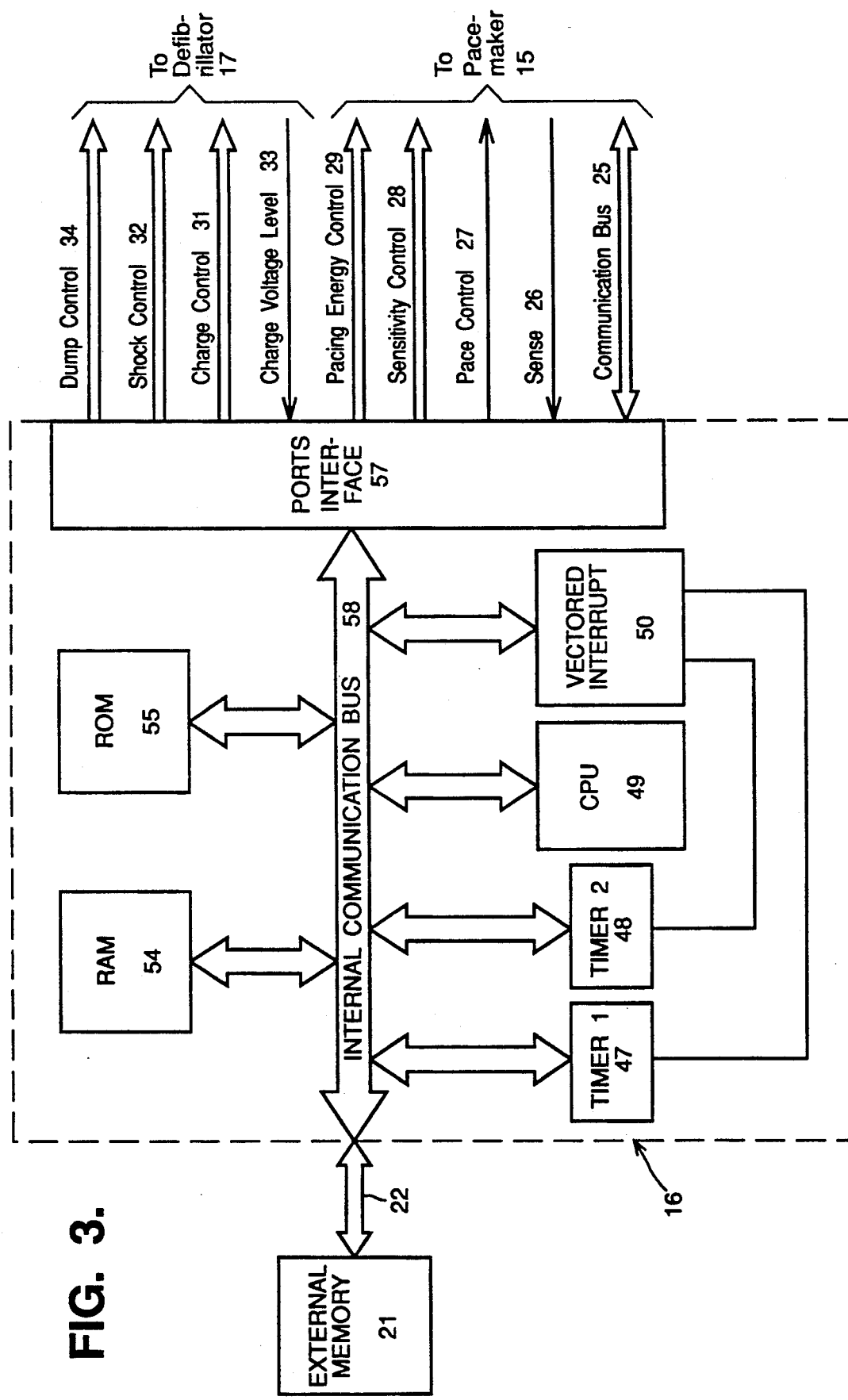
FIG. 3 is a block diagram of a microprocessor utilized in the system of FIG. 1.

Referring now to FIG. 3, microprocessor 16 comprises two 16-bit timers 47 and 48, a CPU 49, a vectored interrupt block 50, a RAM 54, a ROM 55, a ports interface 57 and an internal communications bus 58. RAM 54 acts as a scratch pad and active memory during execution of the various programs stored in ROM 55 and used by microprocessor 16. These programs include system supervisory programs, detection algorithms for detecting various arrhythmias, as well as storage programs for storing, in external memory 21, data concerning the functioning of module 11 and the electrogram provided by cardiac lead 12. Timers 47 and 48 and associated control software implement some timing functions required by microprocessor 16 without resorting entirely to software, thus reducing computational loads on and power dissipation by CPU 49.

Referring to FIGS. 1–3, together, signals received from telemetry circuit 38 permit an external programmer (not shown) to change the operating parameters of pacemaker 15 by supplying appropriate signals to control block 39. Communications bus 25 serves to provide signals indicative of such control to microprocessor 16. Thus, it is also possible for an external programmer to control operation of defibrillator 17 by means of signals provided to microprocessor 16.

Appropriate telemetry commands are utilized to cause telemetry circuit 38 to transmit data to the external programmer. Data stored is read out, by microprocessor 16, on to communications bus 25, through control block 39 in pacemaker 15, and into telemetry circuit 38 for transmission to the external programmer by a transmitter in telemetry circuit 38.

Microprocessor 16 receives various status and/or control inputs from pacemaker 15 and defibrillator 17. During normal pacer operations the input signal to pacemaker 15 is a sense signal on sense line 26 which is used by microprocessor 16 to perform operations such as arrhythmia detection. Microprocessor 16 produces outputs such as the pace control on pace control line 27 which determines the type of pacing to take place as well as the shape of the pacing waveform.

Other pacemaker control outputs generated by microprocessor 16 include a pacing energy control signal on pacing energy control bus 29, which determines the magnitude of the pulse energy, and a sensitivity control signal on sensitivity control bus 28, which determines the sensitivity setting of the sensing circuit.

Microprocessor 16 provides to defibrillator 17 a shock control signal on shock control line 32 which indicates that a shock or micro-shock, is to be delivered to the patient and also designates the shape of the waveform, a dump control signal on dump control line 34 which indicates that a shock or part thereof is to be dumped at an internal load within defibrillator 17, and a charge control signal on charge control bus 31 which determines the voltage level of the shock or microshock to be delivered. Charge voltage level line 30 provides a digital signal representative of charge voltage from an analog to digital converter within defibrillator 17, thus providing a feedback loop which assures that a shock of proper energy level and waveshape is delivered by defibrillator 17.

Figure 4:
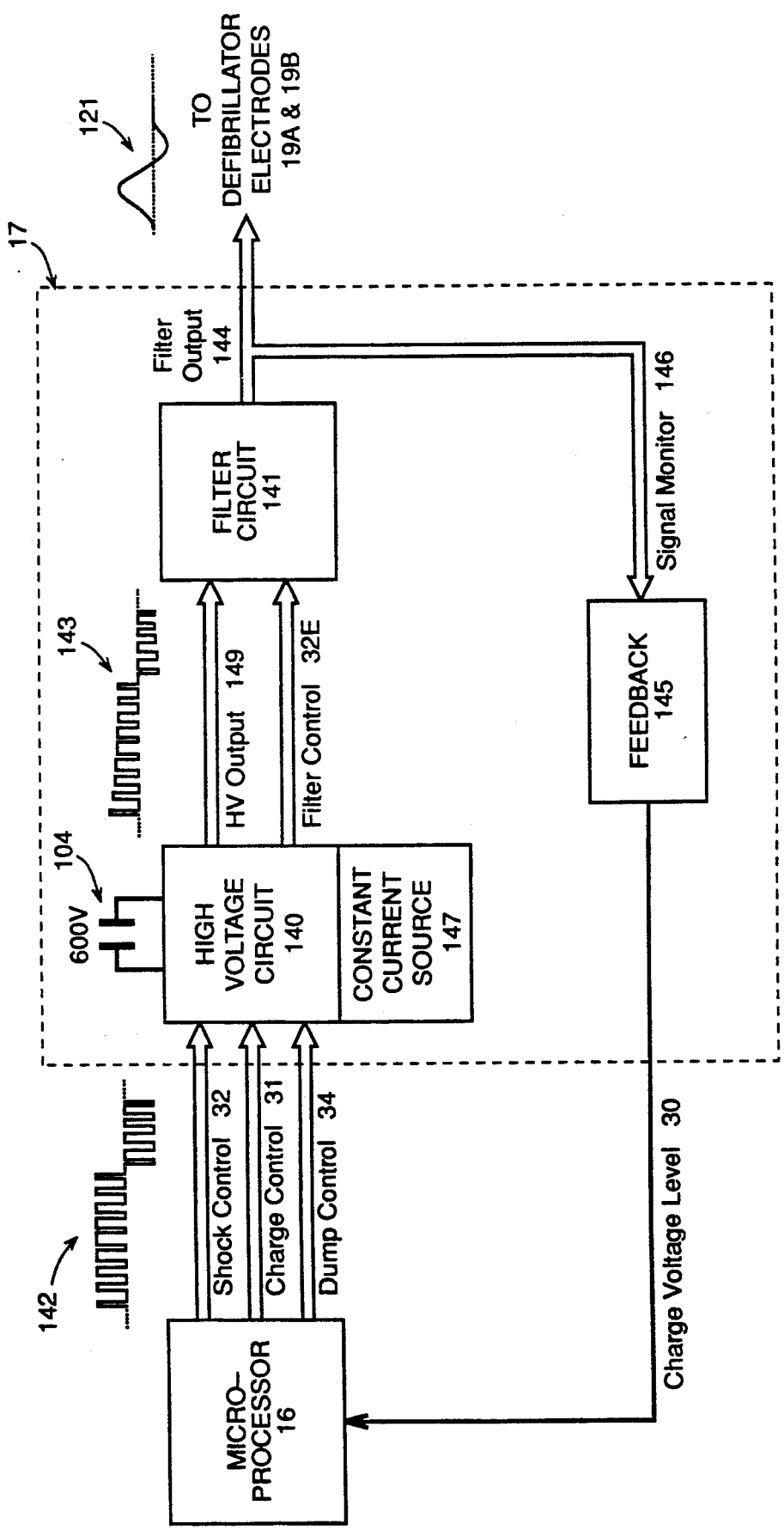
FIG. 4 is a block diagram of a defibrillator utilized in the system of FIG. 1.
Figure 5:
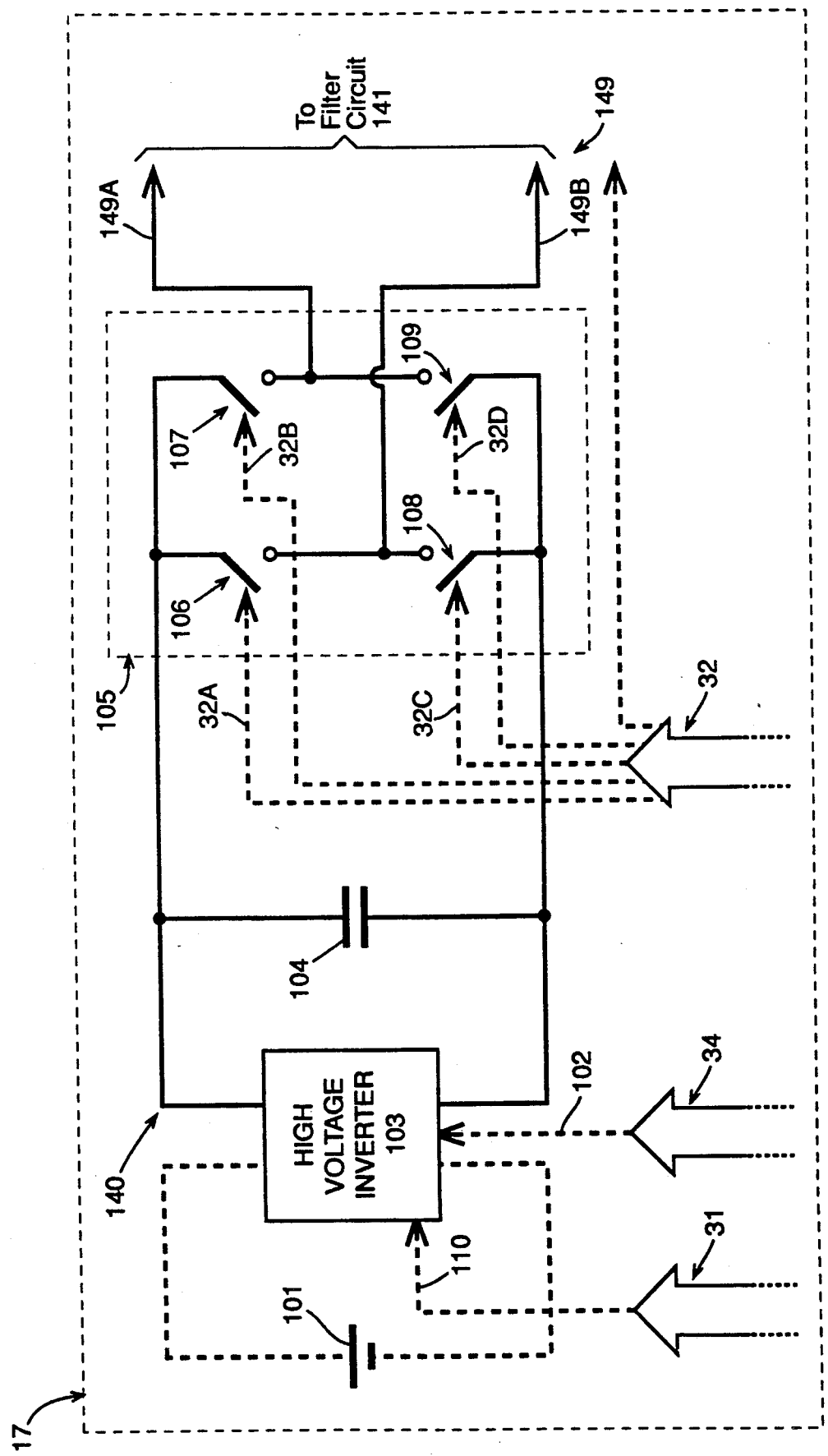
FIG. 5 is a schematic diagram of a high voltage circuit utilized in the defibrillator of FIG. 4.

With reference to FIG. 3, one technique of generating a waveform such as waveform 142 in FIG. 4, is to utilize timer 47 for determining the duration or pulse width of each pulse in the shock control sequence, and timer 48 for determining the duration of each interval between pulses. By varying the durations determined by both of these timers, a shock control waveform can be generated along shock control switches 106–109 (FIG. 5) of defibrillator 17. Switches 106–109, and other similarly illustrated switches shown in FIGS. 6 and 7 that will be discussed hereinafter, are preferably transistors to facilitate the high speed changes in condition they are required to handle. The change in switch conditions ultimately determines the amount of charge per unit time delivered to the patient's heart 14. A similar process could be performed in order to obtain a certain pacing waveform from the pacemaker 15.

Depending on the waveform programmed, timing intervals determined by timers 47 and 48 may need to be derived mathematically by CPU 49 in order to deliver the appropriate signal along shock control bus 32 or pace control line 27. An example of this is the generation of a damped sine wave such as is shown in waveform 121 of FIG. 8. The rate at which damping occurs is dependent on the load impedance of the heart-electrode system (19A, 19B and 14 for defibrillation, or 14 and 12 for pacemaking). Therefore, an impedance measurement of the heart-electrode system may be required to determine the required timing intervals in order to achieve the appropriate waveform.

Referring to FIG. 4, microprocessor 16 sends a control signal waveform 142 on shock control bus 32 to a high voltage circuit 140 in the form of a train of pulses whereby the width of each pulse determines the duration for which the output shock control switches (106, 107, 108 and 109 of FIG. 5) enable current to flow from the charged "tank capacitor" 104 to a filter circuit 141. Similarly, the polarity of the signal waveform 142 on shock control bus 32 controls the polarity of the output signal 143 from the high voltage circuit 140. Filter circuit 141 converts the train of high voltage pulses in output signal 143 from the high voltage circuit 140 into a smooth waveform 121 whereby the shape of the waveform 121 is determined by the amount of charge delivered per unit time by the high voltage pulses 143 into the filter circuit 141. The filter circuit output waveform 121 is applied directly to the defibrillator electrode leads 19A and 19B (FIG. 1) and hence to the heart 14 (FIG. 1). The filter circuit output waveform 121 is also monitored, via signal monitor line 146, by a feedback circuit 145. The charge voltage level output signal 30 is returned from feedback circuit 145 to microprocessor 16 for processing and control of the charge control bus 31, the shock control bus 32 and the dump control bus 34. The dump control bus 34 is used by microprocessor 17 to reduce the charge level on the "tank capacitor" 104 within high voltage circuit 140, if necessary. Conversely, the charge control bus 31 controls the charging of the tank capacitor 104 within the high voltage circuit 140. In another embodiment (not shown), the signal monitoring line 146 could be taken from the output 149 of the high voltage circuit to monitor signal 143, as opposed to monitoring the output signal 144 from filter circuit 141. In a further embodiment (also not shown), an additional feedback path could be incorporated to monitor both the output signal 143 from the high voltage circuit 140 and the output signal 144 from filter circuit 141.

In yet another embodiment of the invention, the high voltage circuit 140 incorporates a constant current source 147 which is used for the measurement of the impedance of the heart 14 together with the electrodes of defibrillation leads 19A and 19B. The mechanism for this is more fully described hereinafter during a discussion pertaining to FIG. 8. However, for the generation of certain waveforms, calculations performed by microprocessor 16, to determine the respective and required durations to be generated by internal timers 47 and 48, require a value for the load impedance of the heart-electrode system (19A, 19B and 14). This is obtained by constant current source 147, upon receiving a signal from microprocessor 17 along shock control bus 32. Upon receiving this signal, constant current source 147 elicits a sub-stimulation threshold current pulse of fixed amplitude (of around 1 milliamp) for a short duration (of around a fraction of a millisecond) and outputs this pulse on high voltage output 149. As the filter characteristics of filter circuit 141 are known, or alternatively as filter circuit 141 can be controlled by shock control bus 32 and filter control bus 32E to cause a signal on high voltage output 149 to bypass the filter circuit 141, a current pulse of known amplitude can be delivered to the defibrillation electrode leads 19A and 19B and hence to the heart 14. Simultaneously, the voltage across defibrillation electrode leads 19A and 19B can be monitored by microprocessor 17 from the signal on charge voltage level line 30, derived from feedback 145 and signal monitor line 146. From the physical law relating voltage (V), current (I) and impedance (Z), V=IZ, the impedance Z of the defibrillation electrodes 19A and 19B as well as the heart 14 can be determined by dividing the measured voltage by the known current amplitude.

Referring to FIG. 5, a schematic block diagram of the preferred embodiment of the high voltage circuit 140 of FIG. 4 has there been illustrated. Battery 101 is the same cell as is used in power supply 18 for the entire pulse module 11 of FIG. 1. Battery 101 supplies power to the high voltage inverter 103 which, when instructed to by a signal on charge control bus 31, charges capacitor 104 to an appropriate voltage. Signals on shock control bus 32 then determine when, and for what duration each of the switches 106, 107, 108, and 109 in switch bank 105 will be closed. It should be noted that switches 106 and 108 would never be instructed to close at the same time, and that switches 107 and 109 would also never be instructed to close at the same time. Output lines 149A and 149B of output 149 deliver a train of high voltage pulses to the filter circuit 141 (FIG. 4) and these pulses then become a smoothed waveform deliverable to the patient's heart 14. Signal line 32E is a filter control line which controls the filter circuit 141, in particular, if and when the filter needs to be by-passed. A signal 102 from dump control bus 34 indicates to the high voltage inverter 103 when (and if) the voltage on capacitor 104 needs to be shunted to an internal load. The signal 102 on bus 34 does not necessarily cause shunting of all of the charge on capacitor 104.

Referring now to FIG. 6 a block diagram of a uniphasic form of the pulse generator 36 of pacemaker 15 (FIG. 2) has there been illustrated. Battery 101 is the same cell as is used in power supply 18 for the entire pulse module 11 of FIG. 1. Battery 101 supplies power to the pacing voltage pump circuit 160 which, in turn, is controlled via switch 164 by a signal 42A on pace control bus 42. Circuit 160 charges capacitor 161 to the required pacing voltage, as controlled by signals on pacing energy control line 29 (FIG. 3). Switch 165, which is controlled by a signal 42B from pacing control bus 42, controls the delivery of the charge accumulated on capacitor 161 to the filter circuit 162 and hence to cardiac lead 12 and the patient's heart 14 (FIG. 2). In the preferred embodiment, switch 165 is opened and closed rapidly and in a predetermined pattern whereby the charge-time relationship is similar to that shown in the left hand portion of the output signal waveform 143 in FIG. 4. As in the case of filter circuit 141 (FIG. 4), filter circuit 162 (FIG. 6) smooths over the accumulating charge being switched in and out by switch 165 to produce on cardiac lead 12 a waveform similar to the left hand portion of waveform 121 of FIG. 4. Filter circuit 162 is similar to filter circuit 141 of FIG. 4, and as such, is controlled by a filter control signal 42C on pacing control bus 42. Similarly, filter circuit 162 has a feedback path 42D along pacing control bus 42 to control block 39 (FIG. 2) which governs signals 42A, 42B and 42C and hence controls the waveshape produced at cardiac lead 12 and hence at the patient's heart 14.

Figure 7:
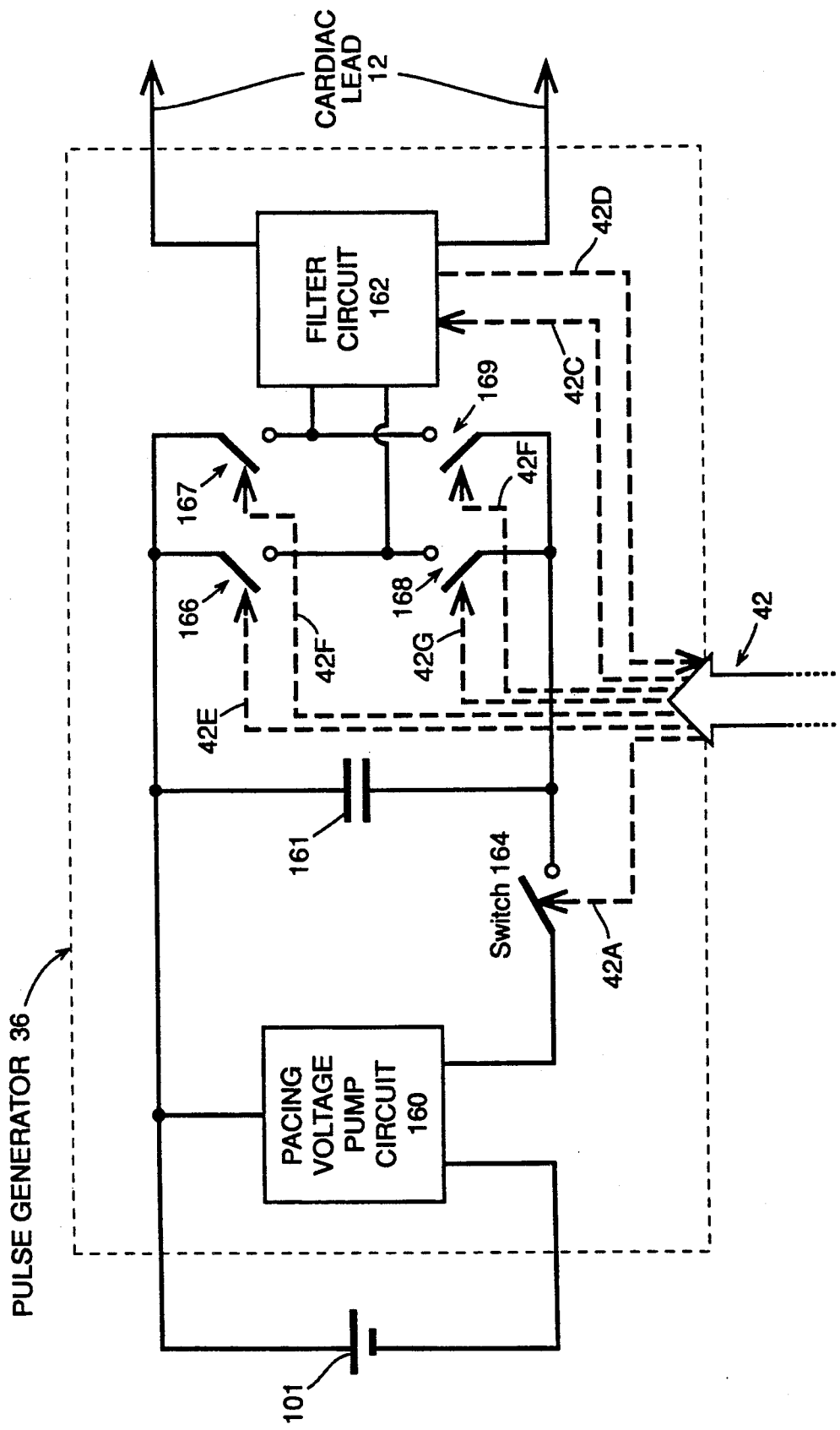
FIG. 7 is a schematic diagram of an alternative embodiment of the pacing pulse generator utilized in the pacemaker of FIG. 2.
Figure 8:
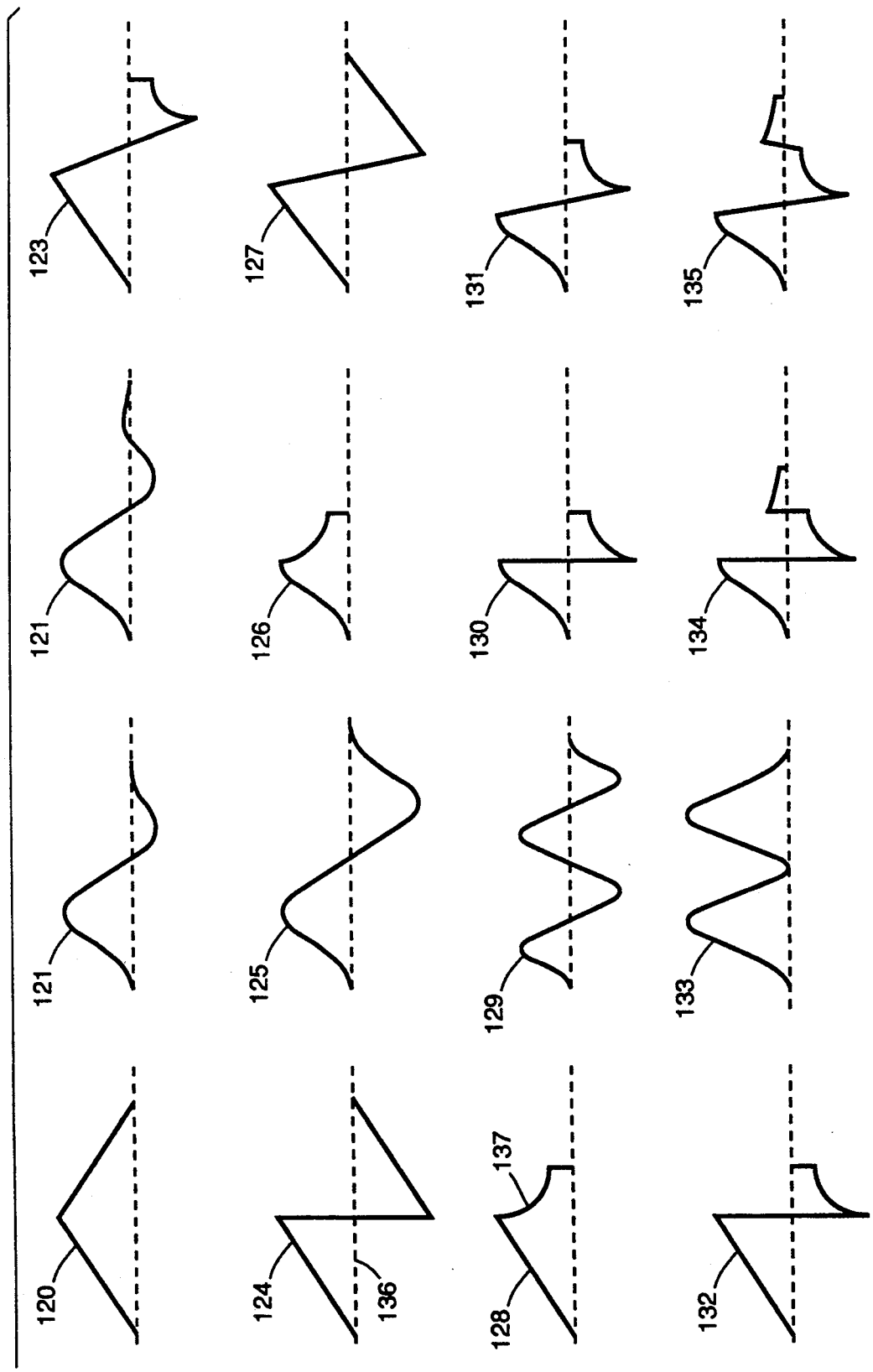
FIG. 8 shows sixteen examples of waveforms that can be produced in either the pacemaker of FIG. 2 or the defibrillator of FIG. 4.

Referring now to FIGS. 7 and 8, an alternative, multi-phasic embodiment of the pulse generator 36 has been illustrated in FIG. 7 and various output waveforms that may be achieved by this pulse generator have been illustrated in FIG. 8. Unlike the embodiment of pulse generator 36 described in FIG. 6, the pulse generator in the FIG. 7 embodiment has the capability of controlling the polarity of any portion of the output pacing waveform Hence, any of the waveforms shown in FIG. 8 can be generated by pulse generator 36, as well as any other waveshape incorporating either or both polarities. This is achieved by controlling a group of switches 166, 167, 168, and 169 by respective control signals 42E, 42F, 42G, and 42H which, in turn, are generated by control block 39 (FIG. 2) and communicated via pacing control bus 42. When signals 42E and 42H close switches 166 and 169, charge flows from capacitor 161 to the filter circuit 162 in one polarity. Conversely, when signals 42F and 42G close switches 167 and 168, charge flows from capacitor 161 to the filter circuit 162 in the other polarity. Hence, control signals 42E and 42G should never close switches 166 and 168 at the same time as this would cause the accumulated charge on capacitor 161 to discharge through the switches 166 and 168, whereby no energy would be delivered to the patient's heart 14. Similarly, control signals 42F and 42H should never close switches 167 and 169 at the same time. As in the case of switch 165 of FIG. 6, the duration during which each of switches 166, 167, 168, and 169 is closed determines the amount of charge to flow from capacitor 161 to filter circuit 162. Hence, the shape of the waveform produced at the output of filter circuit 162 and onto cardiac lead 12 is determined by the relative pulse width and inter-pulse duration of the pulse train produced by opening and closing each of the switches 166, 167, 168, and 169.

Referring now to FIG. 8, sixteen examples of possible waveform outputs 120–135 from the filter circuit 141 of FIG. 4 are shown. Any one of waveforms 120 and 122–135 could replace the signal 121 shown in FIG. 4. Waveform 120 depicts a triangular wave wherein the amplitude and duration are both controlled by microprocessor 16 (FIG. 1). Waveform 124 is a variation of waveform 120 in that it is biphasic and symmetrical about the zero volt line 136. Due to the symmetry of the waveform, it is hence also charge-balanced in that there is no net charge remaining on the interface of defibrillator electrode leads (19A and 19B of FIG. 1) and the heart 14 (FIG. 1). Waveform 128 is another variation of waveform 120; however, the descending portion of the wave at 137 has been replaced by a truncated exponential wave. A variation on waveform 128 is waveform 132 which is biphasic. Waveform 121 depicts a damped sine wave which can be generated by the present invention and is the same waveform as is depicted in FIG. 4. This waveform is biphasic, yet it is not charge balanced. Waveform 122 shows another damped sine wave; however, the damping is less severe than in waveform 121 and, as such, waveform 122 is triphasic. The amount of damping can be controlled by the signal monitor line 146, the feedback circuit 145, the charge voltage level line 30 and the microprocessor 16, all shown in FIG. 4.

As indicated earlier herein, constant current generator 147 within the high voltage circuit 140 of FIG. 4 can be used to generate a current pulse of known amplitude to pass through the filter circuit 141 of FIG. 4, which has known filter characteristics, onto the defibrillation electrode leads 19A and 19B (FIG. 1) and into the heart 14 (FIG. 1). The amplitude of the voltage across the defibrillation electrode leads 19A and 19B can then be monitored by signal monitor line 146, feedback circuit 145, charge voltage level line 30 and microprocessor 16, all shown in FIG. 4. Mathematically dividing the measured voltage level by the known injected current level, yields the magnitude of the electrical impedance of the defibrillation electrode leads 19A and 19B (known to be of fixed and low value) and the heart 14 of FIG. 1. The value of the impedance can be used by microprocessor 16 to determine the pulse train to be generated in order to obtain a resultant specific damping coefficient for the aforementioned sine waves 121 and 122.

Referring again to FIG. 8, waveforms 125, 129 and 133 can be seen to be variations of the sine wave able to be generated by the present invention. Waveforms 126, 130 and 134 can also be seen to be variations of the sine wave wherein the leading edge of each of these waveforms is sinusoidal and the trailing edge forms either a truncated exponential wave of the same polarity (126), a truncated exponential wave of the opposite polarity (130), or a biphasic truncated exponential wave (134).

Waveforms 123, 127, 131 and 135 are variations of waveforms 132, 124, 130 and 134, respectively. For the reasons explained earlier, all of the waveforms in FIG. 8 are designed to eliminate rapidly rising leading edges. It is of further concern that it may be necessary to minimise all rapid transitions. This can be achieved by slowing down the fast edges of the polarity-changeover portions of waveforms 132, 124, 130 and 134, as is shown in waveforms 123, 127, 131 and 135.

It is to be understood that these waveforms, as well as others, could be generated by the pacing pulse generator 36 of FIG. 6, for pacing therapy, as well as by the defibrillator shock and micro-shock pulse waveform shaping circuits of FIG. 4 and 5.

Figure 9:
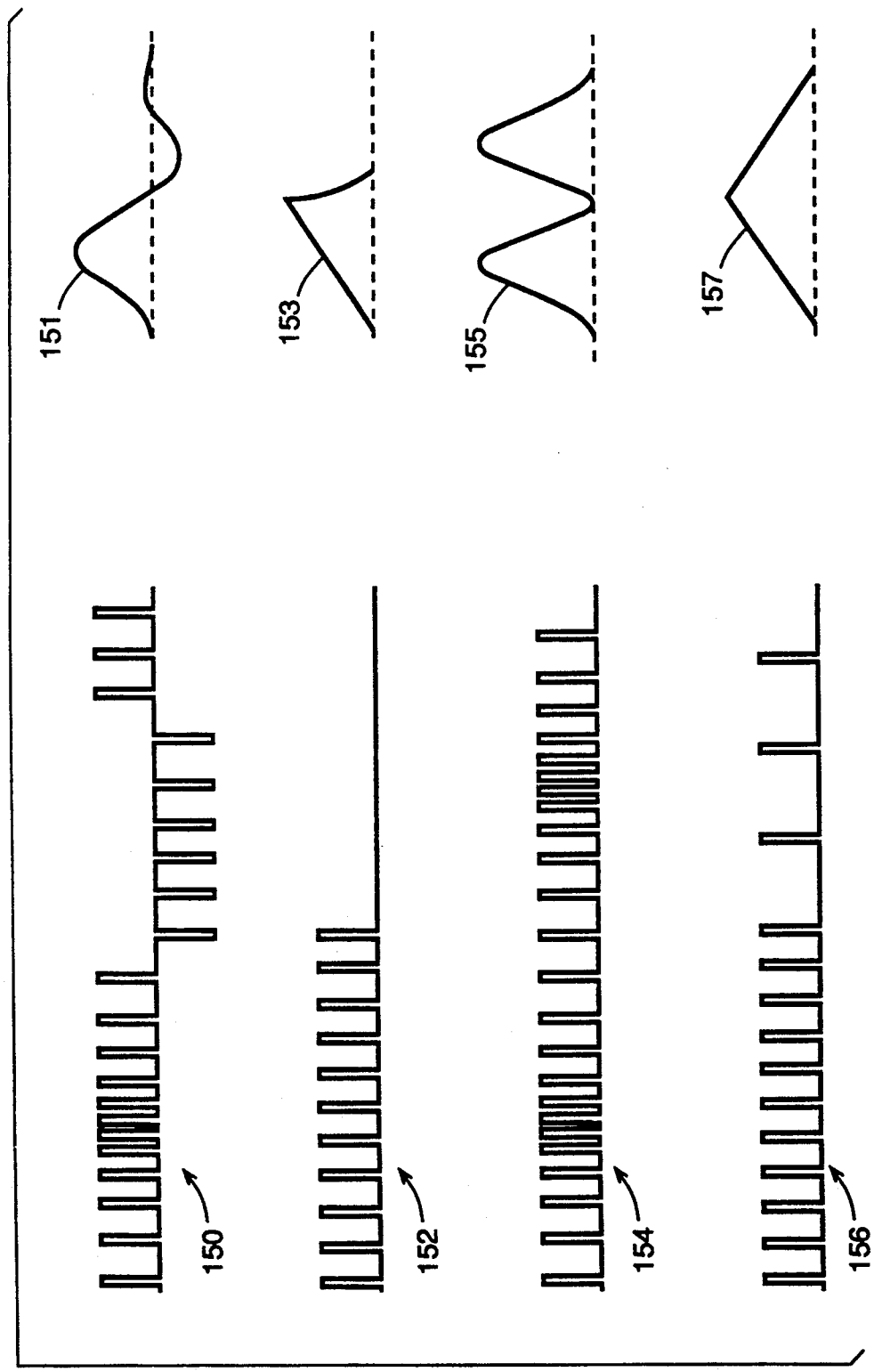
FIG. 9 shows examples of various types of input control signals utilized to obtain corresponding different waveform outputs from the pacemaker of FIG. 2 or the defibrillator of FIG. 4.

Referring now to FIG. 9, there are depicted four examples of pulse trains required to be generated by microprocessor 16 (FIG. 4) and put out on shock control bus 32 (FIG. 4) in order to generate at the output of filter circuit 141 (FIG. 4) the appropriate waveforms shown on the right of each pulse train in FIG. 9. That is, in order to generate the waveform 151 at the output of the filter circuit 141 (FIG. 4), the required output from the microprocessor 16 on shock control bus 32 (FIG. 4) should be of the form shown as pulse train 150. Similarly, to obtain the waveform 153 to be delivered to the heart, a pulse train similar to pulse train 152 would have to be generated by the microprocessor 16 and output along shock control bus 32 (FIG. 4). An example of the pulse train from microprocessor 16 along shock control line 32 (FIG. 4) that would be required in order to obtain the sinusoidal waveform shown diagrammatically at 155 is shown by pulse train 154. Furthermore, to obtain the waveform shown at 157 from the output of the filter circuit 141 (FIG. 4), microprocessor 16 would be required to output along shock control bus 32 a signal similar to that shown at pulse train 156.

It is understood that the pulse trains shown in FIG. 9 are exemplary and are not the only pulse trains that could produce the relevant and desired waveform. A variation on these pulse trains, for example, could be to alter the width of each pulse in the train instead of, or in addition to, the intervals between successive pulses.

It is to be further understood that these waveforms, as well as others, could be generated by the pacing pulse generator 36 of FIG. 6, for pacing therapy, as well as by the defibrillation shock and micro-shock pulse waveform shaping circuit of FIG. 4 and 5.

Various aspects of the invention may be subject to programmability so that a physician may individualize the therapy for a particular patient's own needs. Also by means of appropriate software programming the device may automatically select, from a combination of different parameters, the most effective value of each parameter in order to achieve the most appropriate stimulus. These automatically selected parameters include, but are not limited to: the shape of the pacing pulse waveform for both bradycardia pacing and antitachycardia pacing, including the width of the pulse, the amplitude of the pulse, the polarity of the initial phase of the pulse and the number of phases of the pulse; the shape of the micro-shock waveform for fibrillation and arrhythmia induction, including the width of the micro-shock, the amplitude of the micro-shock, the polarity of the initial phase of the micro-shock and the number of phases of the micro-shock; the shape of the cardioversion or defibrillation shock waveform, including the width of the shock, the amplitude of the shock, the polarity of the initial phase of the shock and the number of phases of the shock; the number of electrodes and the particular electrodes selected from a possible plurality of pacing and cardioversion/defibrillation electrodes connected to the invention, through which either a pacing, micro-shock, cardioversion or defibrillation waveform is to be delivered to the patient's heart, including, but not limited to, endocardial, epicardial and subcutaneous electrodes; whether pacing, micro-shock, cardioversion and defibrillation waveforms are to be delivered to the patient's heart simultaneously, in succession or singly; the number of pacing, micro-shock, cardioversion or defibrillation waveforms to be delivered to the patient's heart; the time interval between the delivery of successive pacing, micro-shock, cardioversion and defibrillation waveforms; whether successive pacing, micro-shock, cardioversion or defibrillation waveforms are to be delivered to the same set of electrodes or to different electrodes from the total plurality of electrodes connected to the invention, including whether the cardioversion/defibrillation circuitry delivers shocks or micro-shocks to the pacing electrodes, and whether the pacing circuitry delivers pacing pulses to the cardioversion or defibrillation electrodes; whether the shape of the pacing, micro-shock, cardioversion or defibrillation waveforms delivered in succession are the same or different; what type of waveform is delivered to the patient's heart each time a waveform is delivered in a succession, where the waveforms of choice are pacing, micro-shock, cardioversion and defibrillation; the timing between the detection of a trigger such as the detection of the R-wave of the ECG or a haemodynamic sensor such as the right ventricular pulse pressure or peak systolic pressure, or other intra-cavitary pressure, intramural pressure, impedance changes, cardiac motion detectors, sonomicrometry, or a combination of these or other electrical, mechanical, chemical, or haemodynamic characteristics known to those skilled in pacemaker and defibrillator technology.

In all embodiments, ranging from single chamber pacemakers which can provide bradycardia support pacing in either the atrium or the ventricle and which may or may not be rate-responsive, to the dual chamber pacemaker/defibrillator which can provide bradycardia and antitachycardia pacing as well as cardioversion, defibrillation therapy and arrhythmia induction in either or both of the atrium and the ventricle and either singly, simultaneously or sequentially, the technique for obtaining the variety of waveforms, some of which are described hence, is to pulse the output of the respective existing pacemaker or cardioverter/defibrillator circuitry and filter the pulsed waveform. By varying the duty cycle of the pulsed waveforms, an endless array of waveshapes is obtainable from the filter.

Although the invention has been described with reference to a particular embodiment, it is to be understood that this embodiment is merely illustrative of the application of the principles of the invention. For example, the principle of the invention applies equally to single chamber defibrillator/pacemaker devices and dual chamber defibrillator/pacemaker devices which incorporate in their therapy both atrial and ventricular bradycardia and/or antitachycardia pacing, whereby the device has the capability of inducing fibrillation and other arrhythmias in both the atrium and the ventricle as well as delivering bradycardia pacing, antitachycardia pacing, cardioversion and/or defibrillation therapy to either the atrium and/or the ventricle of the patient,s heart. Furthermore, the principle of the invention applies equally to pacemaker or defibrillator devices alone, whereby the device could be a single chamber or dual chamber bradycardia and/or antitachycardia pacemaker capable of pacing in either or both of the atrium and ventricle of the heart, or the device could be a single chamber or dual chamber cardioverter/defibrillator capable of cardioversion and/or defibrillation in either or both of the atrium and the ventricle of the heart. In addition, the principle of the device applies equally to the waveform generated by an implantable cardiomyostimulator. Furthermore, other parameters which may be incorporated in the invention are not limited to those disclosed herein either directly or by cross reference. Hence numerous other modifications may be made therein and other arrangements may be devised without departing from the spirit and scope of the invention.

What is claimed is:

1. An implantable device for providing therapy to a patient's inadequately functioning heart, comprising a defibrillation electrode lead system, means for detecting fibrillation of the heart, circuit means including charge storing means for applying electrical therapy to the heart via said electrode lead system, means responsive to the detection of a fibrillation condition for charging said charge storing means to an appropriate energy level for delivering defibrillation therapy to the patient's heart, and means coupled to said circuit means for selectively providing to said defibrillation electrode lead system pulses having at least one of a plurality of different defibrillation waveforms.

2. An implantable device for providing therapy to a patient's inadequately functioning heart, comprising a cardioversion electrode lead system, means for detecting arrhythmias of the heart, circuit means including charge storing means for applying cardioversion therapy to the heart via said electrode lead system, means responsive to the detection of an arrhythmia condition for charging said charge storing means to an appropriate energy level for delivering cardioversion therapy to the patient's heart, and means coupled to said circuit means for selectively providing to said cardioversion electrode lead system pulses having at least one of a plurality of different cardioversion waveforms.

3. An implantable device for providing therapy to a patient's inadequately functioning heart, comprising a pacing electrode lead system, means for detecting a bradycardia condition of the heart, circuit means for applying bradycardia pacing therapy to the heart via said electrode lead system, means responsive to a detected bradycardia condition for supplying power to said circuit means at an appropriate energy level for delivering said bradycardia pacing therapy to the patient's heart, and means coupled to said circuit means for selectively providing to said pacing electrode lead system pulses having at least one of a plurality of different pacing pulse waveforms.

4. An implantable device for providing therapy to an inadequately functioning heart, comprising a pacing electrode lead system, means for detecting a tachycardia condition of the heart, circuit means for applying antitachycardia pacing therapy to the heart via said electrode lead system, means responsive to a detected tachycardia condition for supplying power to said circuit means at an appropriate energy level for delivering said antitachycardia pacing therapy to the patient's heart, and means coupled to said circuit means for selectively providing to said pacing electrode lead system pulses having one or more of a plurality of different pacing pulse waveforms.

5. An implantable device according to any one of claims 1-4, wherein said means for providing a plurality of pulses having any one of a plurality of different waveforms comprises means for generating a selectable train of spaced pulses of electrical energy, and means in series with said train of spaced pulses for smoothing said train of spaced pulses into a discrete single pulse having a continuous waveform.

6. An implantable device according to claim 5, wherein said means for generating a selectable train of spaced pulses of electrical energy includes a plurality of switches in said circuit means.

7. An implantable device according to claim 6, wherein said smoothing means comprise a filter.

8. An implantable device according to claim 7, wherein said continuous waveform is unipolar.

9. An implantable device according to claim 7, wherein said continuous waveform is multipolar.

10. An implantable device according to claim 7, wherein said continuous waveform is monophasic.

11. An implantable device according to claim 7, wherein said continuous waveform is multiphasic.

12. An implantable device for providing therapy to an inadequately functioning heart, comprising a defibrillation electrode lead system, means for detecting fibrillation of the heart, circuit means including charge storage means for applying electrical therapy to the heart via said electrode lead system, means for charging said charge storing means to an appropriate energy level for delivering said defibrillation therapy to the patient's heart, and arrhythmia induction means including means for providing in succession to said defibrillation electrode lead system a plurality of pulses having any one or more of a plurality of different micro-shock waveforms.

13. An implantable device for providing therapy to an inadequately functioning heart, comprising a cardioversion lead system, means for detecting arrhythmias of the heart, circuit means including charge storing means for applying cardioversion therapy to the heart via said electrode lead system, means responsive to the detection of an arrhythmia condition for charging said charge storing means to an appropriate energy level for delivering cardioversion therapy to the patient's heart, and arrhythmia induction means including means for providing in succession to said cardioversion electrode lead system a plurality of pulses having any or more of a plurality different micro-shock waveforms.

14. An implantable device for providing therapy to an inadequately functioning heart, comprising a pacing electrode lead system, means for detecting arrhythmias of the heart, circuit means including charge storing means for applying pacing therapy to the heart via said electrode lead system, means responsive to the detection of an arrhythmia condition for charging said charge storing means to an appropriate energy level for delivering pacing therapy to the patient's heart, and arrhythmia induction means including means for providing in succession to said electrode lead system a plurality of pulses having any one or more of a plurality of different pacing waveforms.

15. An implantable device according to any one of claims 12-14, wherein said means for providing a plurality of pulses having any of a plurality of different waveforms comprises means for generating selectable trains of spaced pulses of electrical energy, and means in series with said trains of spaced pulses for smoothing each of said trains of spaced pulses into a discrete pulse having a continuous waveform.

16. An implantable device according to claim 15, wherein said means for generating selectable trains of spaced pulses of electrical energy includes a plurality of switches in said circuit means.

17. An implantable device according to claim 16, wherein said smoothing means comprises a filter.

18. An implantable device according to claim 17, wherein said continuous waveform is unipolar.

19. An implantable device according to claim 17, wherein said continuous waveform is multipolar.

20. An implantable device according to claim 17, wherein said continuous waveform is monophasic.

21. An implantable device according to claim 17, wherein said continuous waveform is multiphasic.

22. An implantable device according to any one of claims 1-14, wherein at least a portion of the following parameters can be manually programmed into the device: waveform; amplitude of each phase of a wave; width of a waveform; waveform polarity; polarity of each phase of a waveform; phase width for each phase in a given waveform; number of waveform phases; number of waveforms in a series; selection of electrodes for the delivery of waveforms, including pacing electrodes and cardioversion/defibrillation electrodes; selection of electrodes for the delivery of phases of waveforms, including pacing electrodes and cardioversion/defibrillation electrodes; selection of electrodes for the delivery of successive waveforms, including pacing electrodes and cardioversion/defibrillation electrodes; measurement of the transcardiac impedance for the determination of the waveform; timing between a trigger from an electrical or haemodynamic sensor and the delivery of a waveform or sequence of waveforms; and timing between successive waveforms in a sequence.

23. An implantable device according to claim 22, wherein at least a portion of the programming of said parameters into the device is performed automatically by the device.

24. An implantable medical device according to any one of claims 1-14, wherein said waveforms are delivered to any one or more chambers of the heart.

25. An implantable device for providing antiarrhythmia therapy to a patient's inadequately functioning heart, comprising: an electrode lead system adapted to be connected to the patient's heart; circuit means including a capacitor for delivering to the electrode lead system antiarrhythmia therapy in the form of electrical energy; means for detecting an arrhythmia condition of the heart; means responsive to the detection of said arrhythmia condition for charging said capacitor to an appropriate energy level for the arrhythmia condition detected; means responsive to the detection of said arrhythmia condition and operative to couple said circuit means to said electrode lead system for discharging a train of spaced pulses of electrical energy from said charged capacitor to said electrode lead system; and means in series with said train of spaced pulses for smoothing said train of spaced pulses into a discrete single pulse having a continuous waveform.

26. An implantable device according to claim 25, wherein said arrhythmia condition is fibrillation, wherein said electrode lead system is a defibrillation electrode lead system, and wherein said capacitor charging means charges said capacitor to an appropriate level for use in defibrillating said fibrillation.

27. An implantable device according to claim 25, wherein said arrhythmia condition is tachycardia, wherein said electrode lead system is a defibrillation electrode lead system, and wherein said capacitor charging means charges said capacitor to an appropriate level for use in cardioverting said tachycardia.

28. An implantable device according to claim 25, wherein said arrhythmia condition is tachycardia, wherein said electrode lead system is a pacing lead system, and wherein said capacitor charging means charges said capacitor to an appropriate level for use in reverting said tachycardia.

29. An implantable device according to claim 25, wherein said arrhythmia condition is bradycardia, wherein said electrode lead system is a pacing lead system, and wherein said capacitor charging means charges said capacitor to an appropriate level for use in bradycardia support pacing.

30. An implantable device for providing antiarrhythmia therapy to a patient's inadequately functioning heart, comprising: an electrode lead system adapted to be connected to the patient's heart; circuit means for delivering to the electrode lead system antiarrhythmia therapy in the form of electrical energy; means for detecting an arrhythmia condition of the heart; means responsive to the detection of said arrhythmia condition for supplying power to said circuit means at an appropriate energy level for the arrhythmia condition detected; means responsive to the detection of said arrhythmia condition and operative to couple said circuit means to said electrode lead system for discharging a train of spaced pulses of electrical energy from said circuit means to said electrode lead system; and means in series with said train of spaced pulses for smoothing said train of spaced pulses into a discrete single pulse having a continuous waveform.

31. An implantable device according to claim 30, wherein said arrhythmia condition is fibrillation, wherein said electrode lead system is a defibrillation electrode lead system, and wherein said capacitor charging means charges said capacitor to an appropriate level for use in defibrillating said fibrillation.

32. An implantable device according to claim 30, wherein said arrhythmia condition is tachycardia, wherein said electrode lead system is a defibrillation electrode lead system, and wherein said capacitor charging means charges said capacitor to an appropriate level for use in cardioverting said tachycardia.

33. An implantable device according to claim 30, wherein said arrhythmia condition is tachycardia, wherein said electrode lead system is a pacing lead system, and wherein said capacitor charging means charges said capacitor to an appropriate level for use in reverting said tachycardia.

34. An implantable device according to claim 30, wherein said arrhythmia condition is bradycardia, wherein said electrode lead system is a pacing lead system, and wherein said capacitor charging means charges said capacitor to an appropriate level for use in bradycardia support pacing.

35. An implantable device for providing antiarrhythmia therapy to, and inducing arrhythmia in, a patient's inadequately functioning heart, comprising: an electrode lead system adapted to be connected to the patient's heart; circuit means for providing antiarrhythmia therapy to said electrode lead system, said circuit means including means for storing an electrical charge; means coupled to said charge storing means for charging said charge storing means to an appropriate first energy level for use in reverting arrhythmia, and for charging said charge storing means to an appropriate second energy level for selectively inducing arrhythmia in the patient's heart; mean operative to couple said circuit means to said electrode lead system for discharging from said electrical storing means to said electrode lead system a train of spaced pulses of electrical energy at said first energy level for reverting arrhythmia in the patient's heart; means operative to couple said circuit means to said electrode lead system for discharging from said electrical storing means to said electrode lead system a plurality of trains of spaced pulses of electrical energy at said second energy level for inducing arrhythmia in the patient's heart; and means in series with said trains of spaced pulses for smoothing each of said trains of spaced pulses into a discrete pulse having a continuous waveform.

36. An implantable device according to claim 35, wherein said antiarrhythmia therapy comprises defibrillation therapy, wherein said electrode lead system is a defibrillation electrode lead system; wherein said first energy level is an appropriate level for use in defibrillating the patient's heart, and wherein said second energy level is an appropriate level for the smoothing means to form the plurality of trains of spaced pulses discharging from said arrhythmia inducing means into a plurality of successive micro-shocks.

37. A device according to any one of claims 25–36, further including means for varying the spacing between pulses in said train of spaced pulses to thereby vary the continuous waveform of said discrete single pulse.

38. A device according to any one of claims 25–36, further including means for varying the durations of the pulses in said train of spaced pulses to thereby vary the continuous waveform of said discrete single pulse.

39. A device according to anyone of claims 25–36, further including means for varying the polarities of the pulses in said train of spaced pulses to thereby vary the continuous waveform of said discrete single pulse.

40. A device according to anyone of claims 25–36, further including means for varying the spacing between, and the polarities and durations of, the pulses in said train of spaced pulses to thereby vary the continuous waveform of said discrete single pulse.

41. A method for providing antiarrhythmia therapy to a patient's inadequately functioning heart, comprising: providing an implantable device including an arrhythmia detection means, an electrode lead system for delivering antiarrhythmia therapy to the heart, and a circuit having an electrical charge storing means therein for providing antiarrhythmia therapy to the electrode lead system; charging said charge storing means to an appropriate level for providing said antiarrhythmia therapy in response to a detected arrhythmia condition; discharging a train of spaced pulses of electrical energy from the charged electrical charge storing means to the electrode lead system; and smoothing said train of spaced pulses into a discrete single pulse having a continuous waveform prior to its reaching the heart.

42. A method according to claim 41, further including the step of varying the spacing between pulses in said train of spaced pulses to thereby vary the continuous waveform of said discrete single pulse.

43. A method according to claim 41, further including the step of varying the durations of the pulses in said train of spaced pulses to thereby vary the continuous waveform of said discrete single pulse.

44. A method according to claim 41, further including the step of varying the polarities of the pulses in said train of spaced pulses to thereby vary the continuous waveform of said discrete single pulse.

45. A method according to claim 41, further including varying the spacing between, and the polarities and durations of, the pulses in said train of spaced pulses to thereby vary the continuous waveform of said discrete single pulse.

46. A method for inducing fibrillation in and providing defibrillation therapy to a patient's inadequately functioning heart, comprising the steps of: providing an implantable device including a fibrillation detection means, a defibrillation electrode lead system for delivering defibrillation therapy to the patient's heart and a defibrillation circuit having an electrical charge storing means therein for providing defibrillation therapy to the defibrillation electrode lead system; charging said charge storing means to an appropriately high energy level for use in defibrillation therapy in response to a detected tachycardia condition, and to an appropriately low energy level for inducing arrhythmia in the patient's heart at selected other times; discharging from said charge storing means to said defibrillation electrode lead system a train of spaced pulses of electrical energy at said low energy level for inducing arrhythmia in the heart; discharging from said charge storing means to said defibrillation electrode lead system a train of spaced pulses of electrical energy at said high energy level for defibrillating the heart; and smoothing each of said trains of spaced pulses into a discrete single pulse having a continuous waveform prior to its reaching the heart.

47. A method according to claim 46, further including the step of varying the spacing between pulses in said train of spaced pulses to thereby vary the continuous waveform of said discrete single pulse.

48. A method according to claim 46, further including the step of varying the durations of the pulses in said train of spaced pulses to thereby vary the continuous waveform of said discrete single pulse.

49. A method according to claim 46, further including the step of varying the polarities of the pulses in said train of spaced pulses to thereby vary the continuous waveform of said discrete single pulse.

50. A method according to claim 46, further including varying the spacing between, and the polarities and durations of, the pulses in said train of spaced pulses to thereby vary the continuous waveform of said discrete single pulse.

* * * * *